United States Patent [19]

Sharifian et al.

[11] Patent Number: 5,259,934
[45] Date of Patent: Nov. 9, 1993

[54] PROCESS FOR REMOVING ACID FROM A HYDROXYLAMINE SALT SOLUTION CONTAINING EXCESS ACID

[75] Inventors: Hossein Sharifian; Steven R. Wilson, both of Austin, Tex.

[73] Assignee: Sachem, Inc., Austin, Tex.

[21] Appl. No.: 824,021

[22] Filed: Jan. 22, 1992

[51] Int. Cl.$^5$ ................................................ C25B 1/00
[52] U.S. Cl. ................................... 204/101; 204/102; 204/182.4
[58] Field of Search .................... 204/182.4, 101, 102, 204/72

[56] References Cited

U.S. PATENT DOCUMENTS

| | | | |
|---|---|---|---|
| 3,766,038 | 10/1973 | Beck et al. | 204/180 P |
| 4,521,285 | 6/1985 | De Witt et al. | 204/72 |
| 4,601,800 | 7/1986 | Weiss et al. | 204/182.4 |
| 4,645,579 | 2/1987 | Weiss et al. | 204/182.4 |
| 4,849,073 | 7/1989 | Dotson et al. | 204/101 |
| 4,968,394 | 11/1990 | Dotson et al. | 204/101 |

FOREIGN PATENT DOCUMENTS 0266187 5/1988 European Pat. Off. .
2602802 2/1988 France .

Primary Examiner—Donald P. Walsh
Assistant Examiner—Ngoclan T. Mai
Attorney, Agent, or Firm—Renner, Otto, Boisselle & Sklar

[57] ABSTRACT

A process is described for reducing the acid content of a solution comprising a hydroxylamine salt and an acid. In one embodiment, the process comprises the steps of:

(A) providing an electrolysis cell comprising an anolyte compartment containing an anode, a catholyte compartment containing a cathode, said compartments being separated from each other by an anionic membrane;

(B) providing an aqueous solution comprising an acid and water in the anolyte compartment, and an aqueous solution comprising the hydroxylamine, the acid and water in the catholyte compartment;

(C) passing a direct current through the electrolysis cell for a period of time effective to reduce the acid content in the catholyte compartment; and (D) recovering a hydroxylamine salt solution from the catholyte compartment containing a reduced amount of acid.

The process of the present invention results in the recovery of hydroxylamine salt solutions containing significantly reduced amounts of acid.

22 Claims, No Drawings

PROCESS FOR REMOVING ACID FROM A HYDROXYLAMINE SALT SOLUTION CONTAINING EXCESS ACID

TECHNICAL FIELD

The present invention relates to a process for reducing acid content of a solution comprising a hydroxylamine salt and an acid. The invention also relates to a hydroxylamine salt solution obtained by the above method.

BACKGROUND OF THE INVENTION

Hydroxylamine salts may be represented by the formulae:

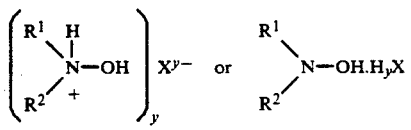

wherein $R^1$ and $R^2$ are independently hydrogen or hydrocarbyl groups, X is an anion of an acid and y is the valence of X. Hydroxylamine salts are compounds which have a variety of applications. For instance, hydroxylamine nitrate may be used as a component of liquid propellant and as a reducing agent in photographic operations. In some of these applications, it is desirable that a hydroxylamine salt solution of high purity is available. Furthermore, it is particularly desirable that a solution containing the hydroxylamine salt also contain a reduced acid content.

There exist several production methods to manufacture hydroxylamine salts. In the case of hydroxylamine nitrate for example, some of these methods include: electrodialysis of hydroxylamine hydrochloride and nitric acid; reaction of hydroxylamine sulfate and barium nitrate; three-step cation exchange process employing hydroxylamine sulfate and nitric acid; and electrolytic reduction of nitric acid. These methods, however, do not provide hydroxylamine salt solutions of high purity which some applications of the compound require. As a result, procedures have been developed to purify the hydroxylamine salt solutions produced by existing methods. Hydroxylamine salt solutions, at present, are purified using thin film evaporators, vacuum-stripping, or other procedures. Nevertheless, there remains a substantial demand for large quantities of high purity hydroxylamine salt solutions. The substantial demand demonstrates that present production methods and purification procedures may be improved.

In light of this substantial demand, French Patent 2,602,802 is directed to an electrolytic process to directly produce high purity solutions of hydroxylamine nitrate. In particular, a process is described for producing by electrolysis a hydroxylamine nitrate solution in an electrochemical cell containing a cathode compartment, an anode compartment and a separator between the cathode compartment and anode compartment. Said process is characterized in that it includes the following operations: (a) introducing a catholyte, essentially containing an aqueous nitric acid solution, in the cathode compartment; (b) introducing an anolyte solution into the anode compartment; (c) electrolyzing the catholyte to a cathode potential between about 0.5 and 1.4 volts compared to the standard calomel electrode, while keeping the temperature of the reaction to the cathode below about 50° C., in order to produce a hydroxylamine solution; and (d) recovering the hydroxylamine nitrate solution from the cathode compartment.

U.S. Pat. No. 3,766,038 relates to a process for the production of cycloalkanone oximes by reaction of cycloalkanones with hydroxylammonium salts or mixtures thereof with ammonium salts and acids in aqueous solution. The free and combined acid is removed from the mixtures by electrodialysis before, during or after the oximation. The reaction of the cycloalkanone to the oxime is preferably carried out in the cathode chamber of an electrodialysis cell. Complete oximation of the cycloalkanone is achieved.

U.S. Pat. No. 4,521,285 relates to an electrolytic cell and a process for removing the halide or other anion from an organic salt having as general formula $A^+X^-$, wherein $A^+$ is an organic cation and $X^-$ is a halide or other anion. Typical compounds of this type are the hydrohalides of nitrogen gases or other salts or hydrosalts of such bases or compounds notably salts (hydrohalides) of quaternary ammonium bases or of amines or amides. However the process herein contemplated may be applied to the removal of anions, e.g., chloride, which are present as an impurity or in combination with the organic compound.

U.S. Pat. No. 4,645,579 relates to aqueous solutions of hydroxylamine which are prepared from aqueous hydroxylammonium salt solutions by electrodialysis by a method in which the aqueous hydroxylammonium salt solution is fed into the middle zone of an electrolysis cell, which is divided into a cathode zone, an anode zone and a middle zone by means of semipermeable membranes, and is electrolyzed, and the catholyte used is an alkali metal hydroxide solution containing ammonia and/or amines.

SUMMARY OF THE INVENTION

A process is described for reducing the acid content of a solution comprising a hydroxylamine salt and an acid. In one embodiment, the process of the present invention comprises the steps of:

(A) providing an electrolysis cell comprising an anolyte compartment containing an anode, a catholyte compartment containing a cathode, said compartments being separated from each other by an anionic membrane;

(B) providing an aqueous solution comprising an acid and water in the anolyte compartment, and an aqueous solution comprising the hydroxylamine salt, the acid and water in the catholyte compartment;

(C) passing a direct current through the electrolysis cell for a period of time effective to reduce the acid content in the catholyte compartment; and (D) recovering a hydroxylamine salt solution from the catholyte compartment containing a reduced amount of acid.

The process of the present invention results in the recovery of a hydroxylamine salt solution containing a significantly reduced amount of acid. The high purity hydroxylamine salt solution produced by the present invention is suitable in applications wherein a highly pure form of the compound is preferred.

DESCRIPTION OF THE PREFERRED EMBODIMENTS

A process is described for reducing the acid content of a solution comprising a hydroxylamine salt and an acid. In one embodiment, the process of the present invention comprises the steps of:

(A) providing an electrolysis cell comprising an anolyte compartment containing an anode, a catholyte compartment containing a cathode, said compartments being separated from each other by an anionic membrane;

(B) providing an aqueous solution comprising an acid and water in the anolyte compartment, and an aqueous solution comprising the hydroxylamine salt, the acid in the catholyte compartment;

(C) passing a direct current through the electrolysis cell for a period of time effective to reduce the acid content in the catholyte compartment; and (D) recovering a hydroxylamine salt solution from the catholyte compartment containing a reduced amount of acid.

The type of electrolysis cell used in the novel process of the present invention may be any of the known electrolysis cells, and the cells may be composed of conventional cell materials which are compatible with the materials being charged into the cells. Since the anode and cathode do not directly enter into the reaction, they also may be made from a variety of materials that do not react with the solutions added to the cells. In a preferred embodiment, the cathode comprises a material with a low overpotential for hydrogen evolution. Suitable cathodes may comprise platinum or nickel. For example, a platinized titanium cathode may be used. The anodes generally may be high purity graphite or platinum electrodes or a titanium electrode coated with an oxide of a material belonging to the platinum group. Another suitable anode includes ruthenized titanium anodes.

The electrolysis is carried out in a cell comprising an anolyte compartment and a catholyte compartment. The compartments are separated by means of an anionic selective membrane. Generally, anionic membranes belong to well known classes of organic commercial polymers, often thermoplastic type, containing polar groups. The anionic selective membrane may be an anion exchange resin or other material, permeable to and capable of transferring anions. The membranes may comprise materials based on the fluorocarbon, polystyrene or polypropylene series. The materials, for instance, may consist of polystyrene which bears on the benzene nucleus dialkylamino groups which in turn, have been converted into quaternary ammonium ions. Additionally, it is preferable to use a durable semipermeable membrane which is acid stable. Specific examples of these membranes are Raipore, and Tosflex from Tosoh Corporation. Other suitable membranes are Neosepta from Tokuyama Soda, Selemion from Asahi Glass, PERMAPLEX A 20, AMFLON series 310 (based on fluorinated polymer substituted with quaternary ammonium) from American Machine and Foundry Co., IONAC MA 3148, MA 3236 and MA 3475 (based on polymer substituted with quaternary ammonium derived from heterogenous polyvinyl chloride) from Ritter-Pfaulder Corp.

The anolyte compartment of the electrolysis cell contains an anode, acid and water. The concentration of the acid in the anolyte compartment is from about 1 to about 6 percent by weight, preferably from about 1 to about 3 percent by weight. The temperature is about 10° C. to about 10° C., preferably about 15° C. to about 25° C.

The catholyte compartment of the electrolysis cell comprises a cathode, hydroxylamine salt, acid and water. The concentration of the hydroxylamine salt in the aqueous solution in the catholyte compartment may be from about 10 to about 25 percent by weight. Preferably the hydroxylamine salt concentration is about 16 to about 18 percent by weight. The concentration of free acid in the solution of the catholyte compartment may be from about 1 to about 6 percent by weight. The term "free acid" as used in this application is intended to refer to the excess acid present in the catholyte solution which is not associated with the hydroxylamine as a salt. Preferably the acid concentration is from about 1 to about 6 percent by weight. The temperature of the catholyte is about 10° C. to about 30° C., preferably about 15° C. to about 25° C. The water, used in the solutions of the present invention, is preferably deionized water, and more preferably very pure deionized water. The solutions of the present invention include the solutions provided to the anolyte and catholyte compartments in addition to any other amounts added to the cell in order to control the concentration of the acid or hydroxylamine salt. For instance, a waterfeed into the anolyte compartment may be employed to manipulate the nitric acid concentration of the solution in the anolyte compartment.

The term "hydrocarbyl" is used herein to include substantially hydrocarbyl groups as well as purely hydrocarbyl groups. The description of these groups as being substantially hydrocarbyl means that they contain no non-hydrocarbyl substituents or noncarbon atoms which significantly affect the hydrocarbyl characteristics or properties of such groups relevant to their uses as described herein. Examples of hydrocarbyl substituents which might be useful in connection with the present invention include: alkyl, alkenyl, alicyclic and aromatic substituents.

The hydroxylamine salts include several embodiments. The amine of the hydroxylamine salt may have hydrogen substituents or hydrocarbyl substituents. In one embodiment, the hydroxylamine salt may be unsubstituted hydroxylamine salt. Specific embodiments of the hydrocarbyl substituted hydroxylamine salt include: diethyl hydroxylamine salt, isopropylhydroxylamine salt and methylhydroxylamine salt.

The acids employed in the present invention are organic and inorganic acids. In one embodiment, the organic acid is formic or acetic acid. In another embodiment, the acid is an inorganic acid. Nonlimiting examples of inorganic acids include: boric acid, hydrochloric acid, nitric acid, perchloric acid, phosphoric acid and sulfuric acid. In one preferred embodiment, the acid in the anolyte compartment is the same as the acid in the catholyte compartment.

The hydroxylamine salt may be represented by the following formulae:

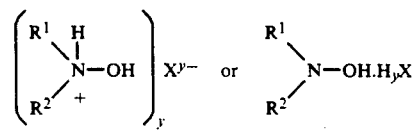

wherein $R^1$ and $R^2$ are independently hydrogen or hydrocarbyl groups containing 1 to about 6 carbon atoms, X is an anion of the acid and y is the valance of X. In one embodiment, the $R^1$ and $R^2$ groups contain 1 to 3 carbon atoms. Specific examples of the hydroxylamine salt include: hydroxylamine nitrate, methylhydroxylamine chloride, diethylhydroxylamine nitrate, isopropylhydroxylamine chloride, methylhydroxylamine sulfate and diethylhydroxylamine acetate.

The electrolysis of the aqueous solution in the catholyte compartment containing the hydroxylamine salt and acid is affected by impressing a direct current voltage between the anode and cathode with a current density of about 55 to about 500 mA/cm$^2$ at about 2 volts to about 8 volts. The current is applied to the electrolysis cell for a period of time effective to reduce the acid content in the catholyte compartment to the desired extent. In one embodiment, the current can be applied until the hydroxylamine salt solution contains no detectable acid.

The electrolytic cell can be operated batchwise or in a continuous operation. Circulation is effected by pumping and/or by gas evolution. In one embodiment, the acid concentration in the anolyte is maintained at a constant concentration by the employment of a waterfeed into the anolyte compartment. Hydroxylamine salt and acid solution can be added periodically or continously to the catholyte compartment to maintain an appropriate concentration.

The process of the present invention may include the introduction of a gas to the electrolytic cell. Generally, the gas is an inert gas and is bubbled through the solution in the catholyte compartment. In one embodiment, the gas is nitrogen or argon.

In one embodiment, the aqueous solution containing the hydroxylamine salt and the acid which is provided in the catholyte compartment in step (B) is prepared by the electrolysis of nitric acid and water. The preparation of the aqueous solution containing hydroxylamine nitrate and nitric acid is conducted in a separate electrolysis cell. The preparation includes passing a direct current through an electrolysis cell which comprises nitric acid and water. In particular, the electrochemical reduction of nitric acid produces hydroxylamine nitrate. An aqueous solution of hydroxylamine nitrate and nitric acid is recovered from the cell. This aqueous solution may be provided in the catholyte compartment in the electrolysis cell of the present invention.

In the present invention, the application of the current in the cell results in a hydroxylamine salt solution in the catholyte compartment containing less acid than the original hydroxylamine salt solution provided in the compartment at the beginning of the process. Although we do not wish to be bound by any theory, one possible explanation of the process is that the direct current flow across the membrane promotes the reduction of water to hydroxide ions and hydrogen, and the hydroxide ions neutralize the acid generating anions such as $NO_3^-$, $Cl^-$, $SO_4^{2-}$, $PO_4^{3-}$, $CH_3COO^-$, etc. The anions migrate through the membrane to the anolyte compartment where they are recovered as acid. One advantage of the process of the present invention is that the acid content in the aqueous hydroxylamine salt solution can be reduced or eliminated without the formation of ammonium nitrate or other byproducts.

The concentration of the acid in the hydroxylamine salt solution recovered from the catholyte compartment is significantly reduced as compared to the acid in the solution originally provided in the catholyte compartment. In particular, the concentration of acid in the solution recovered will be reduced to less than about 2 percent by weight, preferably to less than about 0.6 percent by weight. In other words, a high purity hydroxylamine salt solution is recovered from the catholyte compartment.

The process of the present invention is environmentally and economically beneficial because the waste stream typically associated with such a process is virtually eliminated. It is also possible to reuse the acid recovered from the anolyte compartment. Exposure to poisonous gases is minimized because the process is conducted in solution. Thus, another benefit is the relative safeness of the process.

The following examples illustrate the novel process of the present invention. Unless otherwise indicated in the Examples and elsewhere in the specification and claims, all parts and percentages are by weight, temperatures are in degrees centigrade and pressures are at or near atmospheric.

EXAMPLE 1

An electrolytic cell is prepared containing a platinized titanium cathode, a Ti/RuO$_2$ anode and a Raipore anionic exchange membrane (RAI-5030L). Nitric acid (0.5M) is provided in the anolyte compartment and is maintained at a constant concentration via waterfeed into the anolyte compartment. A solution of hydroxylamine nitrate (2.0M) and nitric acid (1.0M) is provided in the catholyte compartment. Electrolysis is carried out at a current density of about 174 mA/cm$^2$ for about 2.5 hours during which time the catholyte temperature is maintained at 24° C. Analysis of the catholyte solution at the end of this time reveals no detectable ammonium nitrate and elimination of excess nitric acid.

EXAMPLE 2

An electrolytic cell is prepared containing a platinized titanium cathode, a Ti/RuO$_2$ anode and a Neosepta AM-1 anionic selective membrane. Nitric acid (0.5M) is provided in the anolyte compartment and is maintained at a constant concentration via waterfeed into the anolyte compartment. A solution of hydroxylamine nitrate (1.90M) and nitric acid (1.0M) is provided in the catholyte compartment. Electrolysis is carried out at a current density of about 94 mA/cm$^2$ for about five hours during which time the catholyte temperature is maintained at 24° C. Analysis of the catholyte solution at the end of this time reveals no detectable ammonium nitrate and elimination of excess nitric acid.

While the invention has been explained in relation to its preferred embodiments, it is to be understood that various modifications thereof will become apparent to those skilled in the art upon reading this specification. Therefore, it is to be understood that the invention disclosed herein is intended to cover such modifications as fall within the scope of the appended claims.

We claim:
1. A process for reducing the acid content of a solution comprising a hydroxylamine salt and an acid which comprises the steps of:
   (A) providing an electrolysis cell comprising an anolyte compartment containing an anode, a catholyte compartment containing a cathode, said compartments being separated from each other by an anionic membrane;
   (B) providing an aqueous solution comprising an acid and water in the anolyte compartment and aqueous solution comprising the hydroxylamine salt, the acid and water in the catholyte compartment;

(C) passing a direct current through the electrolysis cell for a period of time effective to reduce the acid content in the catholyte compartment; and (D) recovering a hydroxylamine salt solution from the catholyte compartment containing a reduced amount of acid.

2. The process of claim 1 wherein the hydroxylamine salt is represented by the formulae:

$$\left( \begin{array}{c} R^1 \ \ H \\ \phantom{R}\backslash \ | \\ \phantom{R}\phantom{R}N\text{—}OH \\ \phantom{R}/ \ + \\ R^2 \end{array} \right)_y X^{y-} \quad \text{or} \quad \begin{array}{c} R^1 \\ \phantom{R}\backslash \\ \phantom{R}N\text{—}OH.H_yX \\ \phantom{R}/ \\ R^2 \end{array}$$

wherein $R^1$ and $R^2$ are independently hydrogen or hydrocarbyl groups containing 1 to about 6 carbon atoms, X is an anion of the acid and y is the valence of X.

3. The process of claim 2 wherein each R is hydrogen.

4. The process of claim 1 wherein an inert gas is introduced in the catholyte compartment of the electrolysis cell during step (C).

5. The process of claim 1 wherein an inert gas is bubbled through the aqueous solution in the catholyte compartment during step (C).

6. The process of claim 1 wherein the acid is an inorganic acid.

7. The process of claim 1 wherein the acid is acetic acid, hydrochloric acid, nitric acid, perchloric acid, phosphoric acid, sulfuric acid or boric acid.

8. The process of claim 1 wherein the hydroxylamine salt is hydroxylamine nitrate, methylhydroxylamine chloride, isopropylhydroxylamine chloride, methylhydroxylamine sulfate or diethylhydroxylamine acetate.

9. The process of claim 1 wherein the acid in the solution in the catholyte compartment is the same as the acid in the solution in the anolyte compartment.

10. The process of claim 1 wherein the recovered hydroxylamine salt solution contains less than about 2 percent by weight acid.

11. A process for reducing the nitric acid content of a solution comprising hydroxylamine nitrate and nitric acid which comprises the steps of:

(A) providing an electrolysis cell comprising an anolyte compartment containing an anode, a catholyte compartment containing a cathode, said compartments being separated from each other by an anionic membrane;

(B) providing an aqueous solution comprising nitric acid and water in the anolyte compartment, and an aqueous solution comprising hydroxylamine nitrate, nitric acid and water in the catholyte compartment;

(C) passing a direct current through the electrolysis cell for a period of time effective to reduce the nitric acid content in the catholyte compartment; and (D) recovering a hydroxylamine nitrate solution from the catholyte compartment containing a reduced amount of nitric acid.

12. The process of claim 11 wherein an inert gas is bubbled through the solution in the catholyte compartment during step (C).

13. The process of claim 11 wherein the cathode comprises a material with a low overpotential for hydrogen evolution.

14. The process of claim 11 wherein the cathode comprises Pt or Ni.

15. The process of claim 14 wherein the cathode is a platinized titanium cathode.

16. The process of claim 11 wherein the anode comprises Ti.

17. The process of claim 11 wherein the aqueous solution comprising hydroxylamine nitrate and nitric acid provided in the catholyte compartment is prepared by the electrolysis of nitric acid and water.

18. The process of claim 11 wherein the recovered hydroxylamine nitrate solution contains less than about 2 percent by weight nitric acid.

19. A process for reducing the nitric acid content of a solution comprising hydroxylamine nitrate and nitric acid which comprises the steps of:

(A) providing an electrolysis cell comprising an anolyte compartment containing an anode comprising Ti, a catholyte compartment containing a cathode comprising Pt or Ni, said compartments being separated from each other by an anionic membrane;

(B) providing an aqueous solution comprising nitric acid and water in the anolyte compartment, and an aqueous solution comprising the hydroxylamine nitrate, nitric acid and water in the catholyte compartment;

(C) passing a direct current through the electrolysis cell for a period of time effective to reduce the nitric acid content in the catholyte compartment; and (D) recovering a hydroxylamine nitrate solution from the catholyte compartment containing a reduced amount of nitric acid.

20. The process of claim 19 wherein the aqueous solution comprising hydroxylamine nitrate and nitric acid provided in the catholyte compartment is prepared by the electrolysis of nitric acid and water.

21. The process of claim 19 wherein an inert gas is bubbled through the solution in the catholyte compartment during step (C).

22. The process of claim 19 wherein the recovered hydroxylamine nitrate solution contains less than 2 percent by weight nitric acid.

* * * * *